(12) United States Patent
Ho

(10) Patent No.: US 12,042,521 B1
(45) Date of Patent: Jul. 23, 2024

(54) METHOD FOR PRODUCING A COMPLEX COMPOSITION OF TURKEY TAIL MUSHROOM EXTRACT—CHITOSAN

(71) Applicant: Vien Anh Xuan Ho, Ho Chi Minh (VN)

(72) Inventor: Vien Anh Xuan Ho, Ho Chi Minh (VN)

(73) Assignees: Vien Anh Xuan Ho, Ho Chi Minh (VN); Anh Dang Tran, Ho Chi Minh (VN)

( * ) Notice: Subject to any disclaimer, the term of this patent is extended or adjusted under 35 U.S.C. 154(b) by 0 days.

(21) Appl. No.: 18/592,551

(22) Filed: Mar. 1, 2024

(51) Int. Cl.
| | | |
|---|---|---|
| *A61K 36/07* | (2006.01) | |
| *A61K 8/06* | (2006.01) | |
| *A61K 8/9728* | (2017.01) | |
| *A61K 47/36* | (2006.01) | |
| *A61Q 19/00* | (2006.01) | |
| *C12N 1/20* | (2006.01) | |
| C12R 1/07 | (2006.01) | |
| C12R 1/23 | (2006.01) | |
| C12R 1/25 | (2006.01) | |

(52) U.S. Cl.
CPC ............. *A61K 36/07* (2013.01); *A61K 8/06* (2013.01); *A61K 8/9728* (2017.08); *A61K 47/36* (2013.01); *A61Q 19/00* (2013.01); *C12N 1/205* (2021.05); *A61K 2236/17* (2013.01); *A61K 2236/19* (2013.01); *A61K 2236/331* (2013.01); *A61K 2236/37* (2013.01); *A61K 2236/53* (2013.01); *C12R 2001/07* (2021.05); *C12R 2001/23* (2021.05); *C12R 2001/25* (2021.05)

(58) Field of Classification Search
None
See application file for complete search history.

(56) References Cited

U.S. PATENT DOCUMENTS

2016/0037814 A1* 2/2016 Chatani .................. A23L 27/11
426/655

* cited by examiner

*Primary Examiner* — Russell G Fiebig

(57) ABSTRACT

A method for producing a complex composition of turkey tail mushroom extract—chitosan comprising: (i) preparing materials; (ii) mixing the turkey tail mushroom extract ingredient with the emulsifier ingredient to obtain a first homogeneous mixture; (iii) mixing the first homogeneous mixture with the chitosan solution ingredient to obtain a second homogeneous mixture; and (iv) sonicating the second homogeneous mixture to obtain the complex composition of turkey tail mushroom extract—chitosan.

16 Claims, 2 Drawing Sheets

METHOD FOR PRODUCING A COMPLEX COMPOSITION OF TURKEY TAIL MUSHROOM EXTRACT—CHITOSAN

FIELD OF THE INVENTION

The present invention relates to the field of natural product formulations and therapeutic compositions. Specifically, the invention encompasses a complex composition derived from turkey tail mushroom extract and chitosan, produced through a novel and inventive method. The composition finds application in the treatment of various skin conditions and as a hygiene solution, particularly in the context of addressing early mortality syndrome in shrimp as a substitute for antibiotics.

BACKGROUND ART

Turkey tail mushroom has long been recognized for its medicinal properties and has been utilized in traditional medicine for various therapeutic purposes. The mushroom is known for its rich content of bioactive compounds, including polysaccharides such as polysaccharide krestin (PSK) and polysaccharide peptide (PSP), which have demonstrated immunomodulatory and antioxidant properties.

Chitosan, derived from chitin, is another natural substance with widespread applications in various industries, including pharmaceuticals and cosmetics. Its biocompatibility and bioactivity make it an attractive component for formulations aimed at skincare and hygiene.

In recent years, there has been a growing interest in developing novel compositions that harness the benefits of natural products for skincare and health-related applications. The demand for alternatives to synthetic compounds has prompted researchers to explore the potential synergies between different natural ingredients to create formulations with enhanced efficacy.

The existing art reveals several methods for extracting bioactive compounds from mushrooms and chitosan. However, there remains a need for innovative compositions that leverage the unique properties of turkey tail mushroom extract and chitosan in a manner that is not only beneficial for human skincare but also provides a natural solution for challenges faced in aquaculture, such as early mortality syndrome in shrimp.

The prior art has not adequately addressed the specific sequence of steps outlined in the present invention, which ensures the preservation of bioactive components and their synergistic combination in a complex composition.

Therefore, it is necessary to a method for producing a complex composition of turkey tail mushroom extract—chitosan comprising: (i) preparing materials; (ii) mixing the turkey tail mushroom extract ingredient with the emulsifier ingredient to obtain a first homogeneous mixture; (iii) mixing the first homogeneous mixture with the chitosan solution ingredient to obtain a second homogeneous mixture; and (iv) sonicating the second homogeneous mixture to obtain the complex composition of turkey tail mushroom extract—chitosan.

Furthermore, it is necessary to introduce a groundbreaking approach to derive a complex composition from turkey tail mushroom extract and chitosan, with applications ranging from skincare to aquaculture. The inventive method addresses the shortcomings of the prior art and offers a unique solution to challenges in both human health and aquatic resource management.

Finally, what is needed to provide the method for producing a complex composition of turkey tail mushroom extract—chitosan that offers simplified steps, optimized technical specifications, and the potential for industrial-scale application.

This invention provides solutions to achieve the above goals.

SUMMARY OF THE INVENTION

Accordingly, a first aspect of the present invention is to provide a method for producing a complex composition of turkey tail mushroom extract—chitosan comprising steps performed in the following specific order:
(i) preparing materials including: a chitosan solution ingredient, a turkey tail mushroom extract ingredient, and an emulsifier ingredient;
(ii) mixing the turkey tail mushroom extract ingredient with the emulsifier ingredient in a ratio of 1000:(1-3), stirring at a speed of 1200-1500 rpm for 30-50 minutes to obtain a first homogeneous mixture;
(iii) mixing the first homogeneous mixture with the chitosan solution ingredient in a ratio of (4-6):(4-6), stirring at a speed of 1200-1500 rpm for 30-50 minutes to obtain a second homogeneous mixture; and
(iv) sonicating the second homogeneous mixture at 0.15-0.2 kHz, combined with stirring at a speed of 1200-1500 rpm for 30-40 minutes to obtain the complex composition of turkey tail mushroom extract—chitosan.

Another objective of the present invention is to provide the turkey tail mushroom extract ingredient obtained by performing steps (i') to (vi'), comprising:
(i') preparing materials including: a fermentation microorganism solution and a turkey tail mushroom mixture; wherein the fermentation microorganism solution is obtained by mixing a first nutrient broth solution with a second nutrient broth solution and a third nutrient broth solution in a ratio of (1-3):(1-3):(1-3); wherein the turkey tail mushroom mixture is obtained by mixing a first turkey tail mushroom component with a second turkey tail mushroom component, a third turkey tail mushroom component, a fourth turkey tail mushroom component, and a fifth turkey tail mushroom component in a ratio of (1-2):(1-2):(1-2):(1-2):(1-2), then adjusting the brix to achieve 15-20° Bx;
(ii') creating a mixed fermentation solution and a mixed fermentation residue by performing steps (a') to (l'), comprising:
(a') sterilizing the turkey tail mushroom mixture at step (i') at a temperature of 121° C. for 15 minutes to obtain a third temporary mixture;
(b') mixing the fermentation microorganism solution at step (i') with the third temporary mixture in a ratio of 1:(45-55); then fermenting at 30° C.-35° C., combined stirring at a speed of 120 rpm for 35-40 hours to obtain a first fermentation mixture;
(c') filtering the first fermentation mixture to obtain a first fermentation solution and a first fermentation residue; wherein the first fermentation solution is the liquid part and the first fermentation residue is the solid part;
(d') centrifuging the first fermentation solution at a speed of 4000-6000 rpm for 60-90 minutes to obtain a first centrifuged fermentation solution and a second fermentation residue;

(e') mixing the first fermentation residue with the second fermentation residue, then adjusting the Brix to reach 15-20° Bx to obtain a basic mixture;

(f') sterilizing the basic mixture at 121° C. for 15 minutes to obtain a sterile basic mixture;

(g') mixing the fermentation microorganism solution at step (i') with the sterilized basic mixture in a ratio of 1:(45-55); then fermenting at 30° C.-35° C., combined stirring at a speed of 120 rpm for 24-30 hours to obtain a second fermentation mixture;

(h') filtering the second fermentation mixture to obtain a second fermentation solution and a third fermentation residue; wherein the second fermentation solution is the liquid part, and the third fermentation residue is the solid part;

(j') centrifuging the second fermentation solution at a speed of 4000-6000 rpm for 60-90 minutes to obtain a second centrifuged fermentation solution and a fourth fermentation residue;

(k') mixing the first centrifuged fermentation solution with the second centrifuged fermentation solution to obtain the mixed fermentation solution;

(l') mixing the first fermentation residue with the second fermentation residue, the third fermentation residue, and the fourth fermentation residues to obtain the mixed fermentation residue;

(iii') creating a mixed water-extracted solution and a mixed water-extracted residue from the mixed fermentation residue by performing steps (a") to (d"), comprising:

(a") mixing the mixed fermentation residue at step (ii') with water in a ratio of 1:(5-7), boiling at 100° C. for 10-15 minutes, then filtering to obtain a first water-extracted solution and a first water-extracted residue;

(b") mixing the first water-extracted residue with water in a ratio of 1:(5-7), boiling at 100° C. for 10-15 minutes, then filtering to obtain a second water-extracted solution and a second water-extracted residue;

(c") mixing the first water-extracted solution with the second water-extracted solution to obtain the mixed water-extracted solution; and (d") mixing the first water-extracted residue with the second water-extracted residue to obtain the mixed water-extracted residue;

(iv') preparing an alkaline-extracted solution by performing steps (a''') to (e'''), comprising:

(a''') mixing the mixed water-extracted residue at step (iii') with 4% sodium hydroxide (NaOH) in a ratio of 1:(7-8), incubating at 55° C. for 2-3 hours, then filtering to obtain a first alkaline solution and a first alkaline residue;

(b''') mixing the first alkaline residue with 4% sodium hydroxide (NaOH) in a ratio of 1:(7-8), incubating at 55° C. for 2-3 hours, then filtering to obtain a second alkaline solution and a second alkaline residue;

(c''') mixing the first alkaline solution with the second alkaline solution to obtain a mixed alkaline solution;

(d''') neutralizing the mixed alkaline solution with 1N hydrochloric acid (HCl) until the pH reaches 6.8-7.2, then allowing for 12-16 hours to obtain a fourth temporary mixture; and (e''') filtering the fourth temporary mixture, removing the precipitate to obtain the alkaline-extracted solution;

(v') creating a turkey tail mushroom extract sediment by performing steps (a'''') to (d''''), comprising:

(a'''') mixing the fermentation mixture at step (ii") with the mixed water-extracted solution at step (iii") and the alkaline-extracted solution at step (iv") to obtain a fifth temporary mixture;

(b'''') evaporating the fifth temporary mixture at 70° C. until the volume is reduced by 8-10 times to obtain a concentrated mixture;

(c'''') mixing the concentrated mixture with 96% ethanol solution in a ratio of 1:(3-5), precipitating at 4° C. for 12-16 hours to obtain a precipitated concentrated mixture; and (d'''') centrifuging the precipitated concentrated mixture at a speed of 4000-6000 rpm for 30-50 minutes, removing the liquid phase to obtain the turkey tail mushroom extract sediment; and (vi') mixing the turkey tail mushroom extract sediment at step (v') with water in a ratio of 1:(20-30) to obtain the turkey tail mushroom extract ingredient.

Another objective of the present invention is to provide the fermentation microorganism solution is obtained by mixing a first nutrient broth solution with a second nutrient broth solution and a third nutrient broth solution in a ratio of (1-3):(1-3):(1-3); in which, prepare each nutrient broth solution by performing in a specific order from (A') to (C') comprising:

(A') activating a microorganism strain on the Man Rogosa Sharpe (MRS) medium, incubating at a temperature of 30° C.-35° C. for a period of 36-48 hours to obtain an activated microorganism strain;

wherein the microorganism strain used for prepare of the first nutrient broth solution is *Lactobacillus plantarum* (with a designated identifier in the gene bank being JQ937330.1);

wherein the microorganism strain used for prepare of the second nutrient broth solution is *Lactobacillus acidophilus* (with a designated identifier in the gene bank being OK398226.1);

wherein the microorganism strain used for prepare of the third nutrient broth solution is *Bacillus subtilis* (with a designated identifier in the gene bank being KY777343.1);

(B') inoculating a single colony of the activated microorganism strain into a test tube containing 10 ml of LB medium, shaking at 150-200 rpm for 22-24 hours at 30° C.-35° C. to obtain an increased biomass solution; and (C') inoculating the increased biomass solution into LB medium at a ratio of (1-3):100, shaking at 150-200 rpm for 22-24 hours at 30° C.-35° C. to obtain the nutrient broth solution.

A second aspect of the present invention is to provide a complex composition of turkey tail mushroom extract—chitosan produced by the method according to the first aspect for use in the treatment of a skin condition, or hygiene solution, or cosmetic, or functional foods, or antiviral products, or antibacterial products, or dietary supplements, or oral care products, or aquaculture, or agriculture, and livestock products, clinical and medical device/products in this subject.

wherein the treatment of the skin condition is in the forms including face lotion, face wash, sunscreen lotion, body lotion, bath lotion, shampoo, acne treatment, and burned skin; and wherein the hygiene solution in a subject is for lady care and men's hygiene.

Finally, a third aspect of the present invention is to provide a complex composition of turkey tail mushroom extract—chitosan produced by the method according to the first aspect for use in the treatment of an early mortality syndrome (EMS) in shrimp as a replacement for antibiotics.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWING

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the appended claims.

Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

It should be noted that mixing machine/device, centrifuge machine/device, filtering machine/device, fermenter machine/device etc., and other similar machines/devices are well-known in the fields of food processing, biochemistry, and biotechnology. Therefore, detailed descriptions and operating principles of these machines/devices are not provided to avoid obscuring unnecessary aspects of the invention.

It should be noted that the term "turkey tail mushroom" as referenced in the invention refers to fungi belonging to genera including *Trametes* and *Pycnoporus*.

Figure 1:
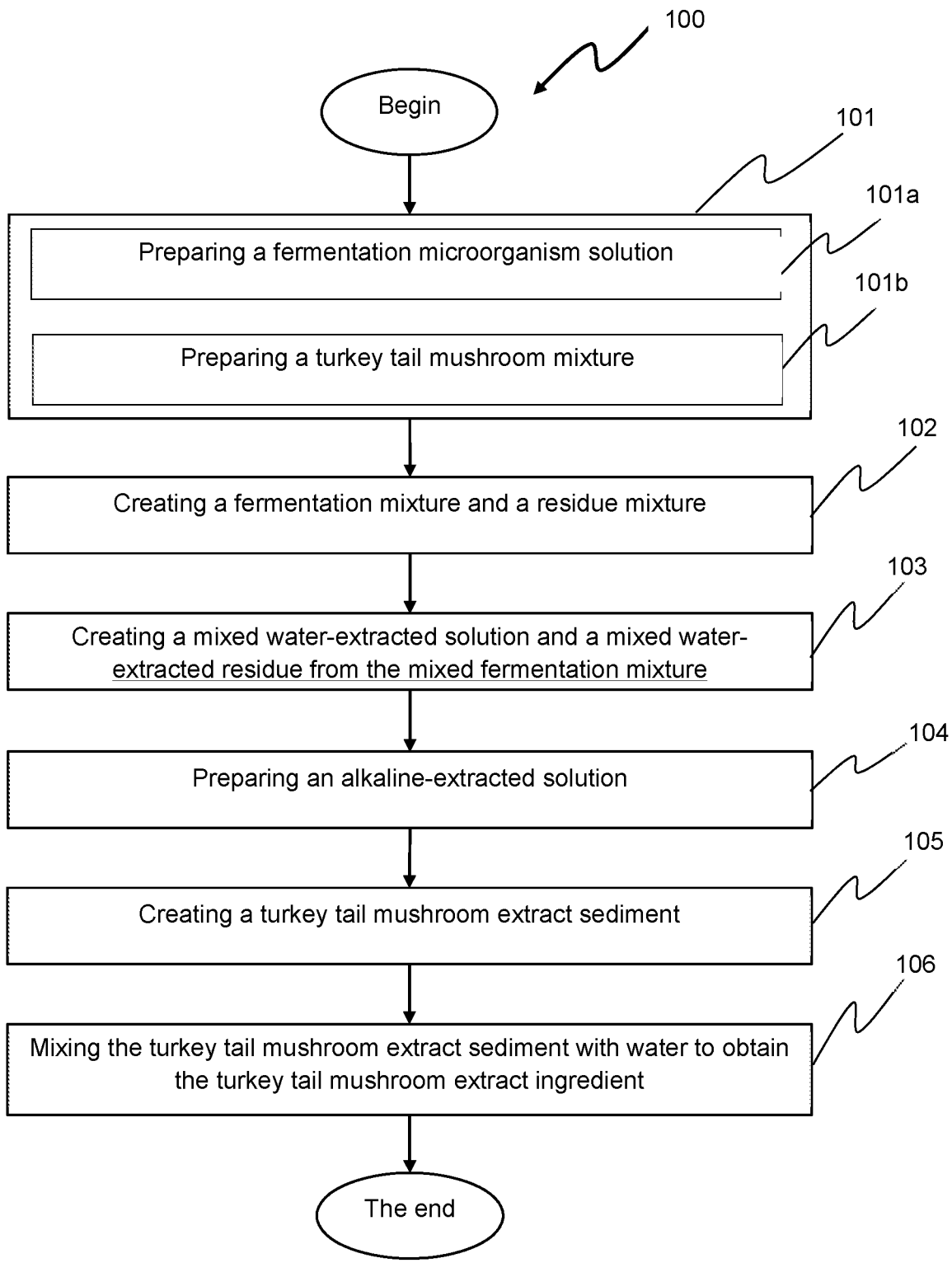
FIG. 1 is a flowchart illustrated a process of preparing the turkey tail mushroom extract ingredient in accordance with an exemplary embodiment of the present invention.

One embodiment of the invention is now described with reference to FIG. 1. FIG. 1 illustrates a process of preparing the turkey tail mushroom extract ingredient 100 ("process 100") in accordance with an exemplary embodiment of the present invention. The process 100 begins with at step 101 preparing materials includes a step 101a to prepare a fermentation microorganism solution, and a step 101b to prepare a turkey tail mushroom mixture.

At step 101a, the fermentation microorganism solution is obtained by mixing a first nutrient broth solution with a second nutrient broth solution and a third nutrient broth solution in a ratio of (1-3):(1-3):(1-3).

In the present invention, prepare each said nutrient broth solution by performing in a specific order from (A') to (C') comprising:

(A') activating a microorganism strain on the Man Rogosa Sharpe (MRS) medium, incubating at a temperature of 30° C.-35° C. for a period of 36-48 hours to obtain an activated microorganism strain;

(B') inoculating a single colony of the activated microorganism strain into a test tube containing 10 ml of LB medium, shaking at 150-200 rpm for 22-24 hours at 30° C.-35° C. to obtain an increased biomass solution; and (C') inoculating the increased biomass solution into LB medium at a ratio of (1-3):100, shaking at 150-200 rpm for 22-24 hours at 30° C.-35° C. to obtain the nutrient broth solution.

According to the preferred embodiment of the present invention, at step (A') the microorganism strain used for prepare of the first nutrient broth solution is *Lactobacillus plantarum* (with a designated identifier in the gene bank being JQ937330.1) that listed in Table 1 below.

According to the preferred embodiment of the present invention, at step (A') the microorganism strain used for prepare of the second nutrient broth solution is *Lactobacillus acidophilus* (with a designated identifier in the gene bank being OK398226.1) that listed in Table 1 below.

According to the preferred embodiment of the present invention, at step (A') the microorganism strain used for prepare of the third nutrient broth solution is *Bacillus subtilis* (with a designated identifier in the gene bank being KY777343.1) that listed in Table 1 below.

TABLE 1

Strains of microorganisms used for prepare of three type of nutrient broth solution according to the embodiment of the invention

| Name of | Genus | Type species | Identifiers |
|---|---|---|---|
| The first nutrient broth solution | *Lactobacillus* | *Lactobacillus plantarum* | JQ937330.1 |
| The second nutrient broth solution | | *Lactobacillus acidophilus* | OK398226.1 |
| The third nutrient broth solution | *Bacillus* | *Bacillus subtilis* | KY777343.1 |

According to the preferred embodiment of the present invention, the fermentation microorganism solution comprising *Lactobacillus plantarum* having at least $1\times10^9$ CFU/mL, *Lactobacillus acidophilus* having at least $1\times10^9$ CFU/mL and *Bacillus subtilis* having at least $1\times10^9$ CFU/mL.

At step 101b, the turkey tail mushroom mixture is obtained by mixing a first turkey tail mushroom component with a second turkey tail mushroom component, a third turkey tail mushroom component, a fourth turkey tail mushroom component, and a fifth turkey tail mushroom component in a ratio of (1-2):(1-2):(1-2):(1-2):(1-2), then adjusting the brix to achieve 15-20° Bx.

According to the preferred embodiment of the present invention, the ratio of the first turkey tail mushroom component with the second turkey tail mushroom component, the third turkey tail mushroom component, the fourth turkey tail mushroom component, and the fifth turkey tail mushroom component is 1:2:2:2:1.

According to the preferred embodiment of the present invention, the turkey tail mushroom mixture containing at least 0.2 g/Kg polysaccharide including polysaccharide krestin, and polysaccharide peptide.

In the present invention, prepare each said turkey tail mushroom component by performing in a specific order from (a) to (f) comprising:
- (a) selecting a mature fruiting bodies of the turkey tail mushroom;
- (b) harvesting mushroom tissue from the mature fruiting bodies of the turkey tail mushroom with an area ranging from 5-10 mm², inoculating onto a petri dish containing a isolation medium, and then incubating in darkness at 28° C.-30° C. for 4-6 days to obtain a turkey tail mushroom strain;
  - wherein the isolation medium comprising: potatoes having 200 g/L, glucose having 20 g/L, potassium dihydrogen phosphate ($KH_2PO_4$) having 3 g/L, magnesium sulfate ($MgSO_4$) having 1.5 g/L, and agar having 20 g/L;
- (c) inoculating the turkey tail mushroom strain into an erlenmeyer flask containing 100-150 mL of an activation medium, shaking at 120-150 rpm for 4-6 days at 25° C.-27° C. to obtain an activated turkey tail mushroom strain;
  - wherein the activation medium comprising: glucose having 10 g/L, malt extract having 3 g/L, peptone having 2 g/L, yeast extract having 2 g/L, asparagine having 1 g/L, potassium dihydrogen phosphate ($KH_2PO_4$) having 2 g/L, magnesium sulfate ($MgSO_4$) having 1 g/L, and thiamine having 1 mg/L;
- (d) inoculating the activated turkey tail mushroom strain into a biomass growth medium at a ratio of (1-5):1000, cultivating with agitation at 120-150 rpm for 6-8 days at 25° C.-27° C. to obtain a second temporary mixture;
  - wherein the biomass growth medium comprising: glucose having 30 g/L, peptone having 4 g/L, magnesium sulfate ($MgSO_4$) having 0.5 g/L, and potassium dihydrogen phosphate ($KH_2PO_4$) having 1 g/L;
- (e) filtering the second temporary mixture, removing the liquid portion to obtain a turkey tail mushroom biomass; and
- (f) drying the turkey tail mushroom biomass at 45° C.-50° C. until reaching a moisture content of 10-12% to obtain the turkey tail mushroom component.

According to the preferred embodiment of the present invention, at step (a) the mature fruiting bodies used for prepare of the first turkey tail mushroom component is *Trametes versicolor* (L.) Pilat.

According to the preferred embodiment of the present invention, at step (a) the mature fruiting bodies used for prepare of the second turkey tail mushroom component is *Trametes versicolor* (L.) Lioud (1920).

According to the preferred embodiment of the present invention, at step (a) the mature fruiting bodies used for prepare of the third turkey tail mushroom component is *Trametes sanguinea* (L.) Imazeki.

According to the preferred embodiment of the present invention, at step (a) the mature fruiting bodies used for prepare of the fourth turkey tail mushroom component is *Trametes versicolor* BRG04.

According to the preferred embodiment of the present invention, at step (a) the mature fruiting bodies used for prepare of the fifth turkey tail mushroom component is *Pycnoporus sanguineus* (L.: Fr.) Murrill.

Still with FIG. 1, at step 102, creating a mixed fermentation solution and a mixed fermentation residue by performing steps (a') to (l'), comprising:
- (a') sterilizing the turkey tail mushroom mixture at step 101 at a temperature of 121° C. for 15 minutes to obtain a third temporary mixture;
- (b') mixing the fermentation microorganism solution at step 101 with the third temporary mixture in a ratio of 1:(45-55); then fermenting at 30° C.-35° C., combined stirring at a speed of 120 rpm for 35-40 hours to obtain a first fermentation mixture;
- (c') filtering the first fermentation mixture to obtain a first fermentation solution and a first fermentation residue; wherein the first fermentation solution is the liquid part and the first fermentation residue is the solid part;
- (d') centrifuging the first fermentation solution at a speed of 4000-6000 rpm for 60-90 minutes to obtain a first centrifuged fermentation solution and a second fermentation residue;
- (e') mixing the first fermentation residue with the second fermentation residue, then adjusting the Brix to reach 15-20° Bx to obtain a basic mixture;
- (f') sterilizing the basic mixture at 121° C. for 15 minutes to obtain a sterile basic mixture;
- (g') mixing the fermentation microorganism solution at step (i') with the sterilized basic mixture in a ratio of 1:(45-55); then fermenting at 30° C.-35° C., combined stirring at a speed of 120 rpm for 24-30 hours to obtain a second fermentation mixture;
- (h') filtering the second fermentation mixture to obtain a second fermentation solution and a third fermentation residue; wherein the second fermentation solution is the liquid part, and the third fermentation residue is the solid part;
- (j') centrifuging the second fermentation solution at a speed of 4000-6000 rpm for 60-90 minutes to obtain a second centrifuged fermentation solution and a fourth fermentation residue;
- (k') mixing the first centrifuged fermentation solution with the second centrifuged fermentation solution to obtain the mixed fermentation solution; and
- (l') mixing the first fermentation residue with the second fermentation residue, the third fermentation residue, and the fourth fermentation residues to obtain the mixed fermentation residue.

According to embodiment of the present invention, the mixed fermentation solution containing polysaccharide having a concentration is 4-6 times higher than the turkey tail mushroom mixture at step 101b; in which said polysaccharide including polysaccharide krestin, and polysaccharide peptide.

According to the preferred embodiment of the present invention, the mixed fermentation solution containing polysaccharide peptide having a concentration is 4-6 times higher than the turkey tail mushroom mixture at step 101b.

According to the preferred embodiment of the present invention, the mixed fermentation solution containing polysaccharide krestin having a concentration is 4-6 times higher than the turkey tail mushroom mixture at step 101b.

According to the preferred embodiment of the present invention, the mixed fermentation solution comprising further lucidenic acid N having 0.03-0.05 mg/g, lucidenic acid E2 having 0.01-0.03 mg/g, lucidadiol having 0.4-0.8 mg/g, and ergosterol having 2.2-4.6 mg/g.

At step 103, creating a mixed water-extracted solution and a mixed water-extracted residue from the mixed fermentation mixture by performing steps (a") to (d"), comprising:
- (a") mixing the mixed fermentation residue at step 102 with water in a ratio of 1:(5-7), boiling at 100° C. for 10-15 minutes, then filtering to obtain a first water-extracted solution and a first water-extracted residue;
- (b") mixing the first water-extracted residue with water in a ratio of 1:(5-7), boiling at 100° C. for 10-15 minutes, then filtering to obtain a second water-extracted solution and a second water-extracted residue;

(c") mixing the first water-extracted solution with the second water-extracted solution to obtain the mixed water-extracted solution; and (d") mixing the first water-extracted residue with the second water-extracted residue to obtain the mixed water-extracted residue.

At step 104, preparing an alkaline-extracted solution by performing steps (a''') to (e'''), comprising:

(a''') mixing the mixed water-extracted residue at step 103 with 4% sodium hydroxide (NaOH) in a ratio of 1:(7-8), incubating at 55° C. for 2-3 hours, then filtering to obtain a first alkaline solution and a first alkaline residue;

(b''') mixing the first alkaline residue with 4% sodium hydroxide (NaOH) in a ratio of 1:(7-8), incubating at 55° C. for 2-3 hours, then filtering to obtain a second alkaline solution and a second alkaline residue;

(c''') mixing the first alkaline solution with the second alkaline solution to obtain a mixed alkaline solution;

(d''') neutralizing the mixed alkaline solution with 1N hydrochloric acid (HCl) until the pH reaches 6.8-7.2, then allowing for 12-16 hours to obtain a fourth temporary mixture; and (e''') filtering the fourth temporary mixture, removing the precipitate to obtain the alkaline-extracted solution.

At step 105, creating a turkey tail mushroom extract sediment by performing steps (a'''') to (d''''), comprising:

(a'''') mixing the fermentation mixture at step (ii'') with the mixed water-extracted solution at step (iii'') and the alkaline-extracted solution at step 104 to obtain a fifth temporary mixture;

(b'''') evaporating the fifth temporary mixture at 70° C. until the volume is reduced by 8-10 times to obtain a concentrated mixture;

(c'''') mixing the concentrated mixture with 96% ethanol solution in a ratio of 1:(3-5), precipitating at 4° C. for 12-16 hours to obtain a precipitated concentrated mixture; and (d'''') centrifuging the precipitated concentrated mixture at a speed of 4000-6000 rpm for 30-50 minutes, removing the liquid phase to obtain the turkey tail mushroom extract sediment.

Finally, at step 106, mixing the turkey tail mushroom extract sediment at step 105 with water in a ratio of 1:(20-30) to obtain the turkey tail mushroom extract ingredient.

According to the preferred embodiment of the present invention, the turkey tail mushroom extract ingredient containing chemical components includes polysaccharide krestin (PSK), polysaccharide peptide (PSP), lucidenic acid N, lucidenic acid E2, lucidadiol, and ergosterol.

Figure 2:
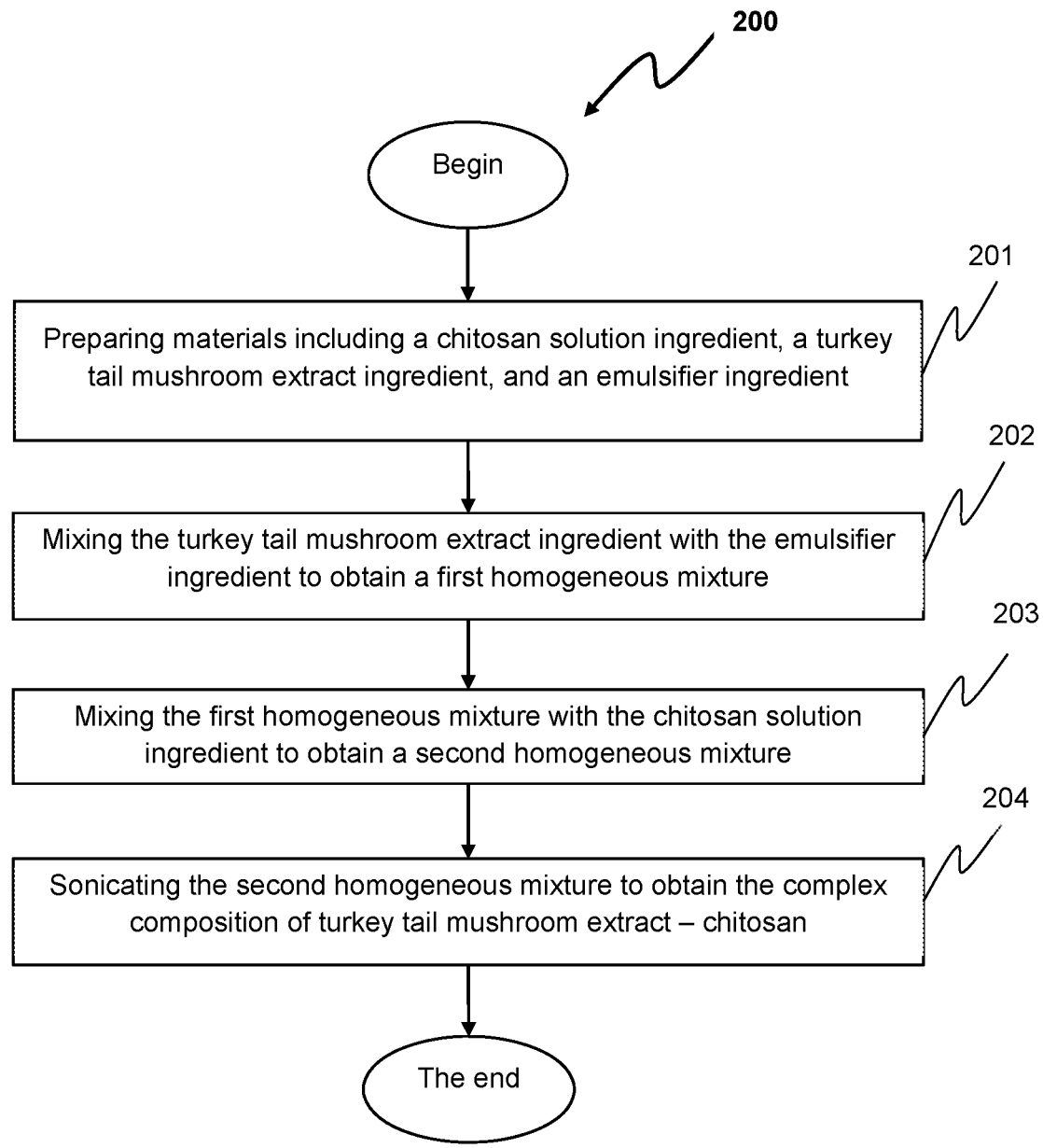
FIG. 2 is a flowchart illustrated a method for producing a complex composition of turkey tail mushroom extract—chitosan in accordance with an exemplary embodiment of the present invention.

Now referring to FIG. 2, a method for producing a complex composition of turkey tail mushroom extract—chitosan 200 ("method 200") according to the embodiment of the present invention. Method 200 begins with at step 201 preparing materials including: a chitosan solution ingredient, a turkey tail mushroom extract ingredient, and an emulsifier ingredient.

In the present invention, the emulsifier ingredient is selected from one of the emulsifier groups consisting of sucrose ester, monoglyceride, triglyceride, and lecithin.

In the present invention, the chitosan solution ingredient is obtained by performing steps (A) to (C), comprising:

(A) preparing materials including: a chitosan component, a 95% acetic acid solution, and a water component; wherein the chitosan component has a minimum deacetylation degree of 85%;

(B) mixing the chitosan component with the water component in a ratio of 1:(20-30), stirring at 150-200 rpm for 30-40 minutes at 25° C.-35° C. to obtain a first temporary mixture; and (C) mixing the first temporary mixture with the 95% acetic acid solution in a ratio of 1:(60-70), stirring at 100-120 rpm for 12-16 hours at 25° C.-35° C. to obtain the chitosan solution ingredient.

In the present invention, the turkey tail mushroom extract ingredient is prepared according to the process 100 described above.

Still with FIG. 2, at step 202, mixing the turkey tail mushroom extract ingredient with the emulsifier ingredient in a ratio of 1000:(1-3), stirring at a speed of 1200-1500 rpm for 30-50 minutes to obtain a first homogeneous mixture.

At step 203, mixing the first homogeneous mixture with the chitosan solution ingredient in a ratio of (4-6):(4-6), stirring at a speed of 1200-1500 rpm for 30-50 minutes to obtain a second homogeneous mixture.

Finally, at step 204, sonicating the second homogeneous mixture at 0.15-0.2 kHz, combined with stirring at a speed of 1200-1500 rpm for 30-40 minutes to obtain the complex composition of turkey tail mushroom extract—chitosan.

According to another embodiment, the invention disclosing further a complex composition of turkey tail mushroom extract—chitosan produced by the method 200 for use in the treatment of a skin condition, or hygiene solution, or cosmetic, or functional foods, or antiviral products, or antibacterial products, or dietary supplements, or oral care products, or aquaculture, or agriculture, and livestock products, clinical and medical device/products in this subject.

According to the preferred embodiment of the present invention, the treatment of the skin condition is in the forms including face lotion, face wash, sunscreen lotion, body lotion, bath lotion, shampoo, acne treatment, and burned skin.

In the following, in order to facilitate the understanding of the present solution, some proper nouns appearing in the following embodiments of the present application are explained:

The term "face lotion" refers to a cosmetic product specifically formulated for application to the facial skin. Typically used to moisturize, hydrate, and nourish the skin, face lotion aims to improve skin texture and address specific concerns such as dryness, aging, or acne.

The term "face wash" refers to a skincare product designed to cleanse the facial skin. It is typically used to remove dirt, oil, makeup, and other impurities from the skin's surface, providing a clean and refreshed feeling.

The term "sunscreen lotion" is a type of skincare product specifically formulated to protect the skin from harmful UV rays emitted by the sun. It is applied topically to the skin and works by absorbing or reflecting the sun's ultraviolet radiation, thereby preventing sunburn, premature aging, and reducing the risk of skin cancer.

The term "body lotion" refers to a skincare product intended for use on the skin, usually applied after bathing or showering. It's formulated to moisturize, hydrate, and nourish the skin on different body parts, except the face. Body lotion contributes to skin health by preventing dryness, enhancing skin texture, and improving its overall look and feel.

The term "bath lotion" refers to a skincare product designed for use during bathing. Typically added to bathwater, it is formulated to provide hydration and nourishment to the skin while soaking in the bath. Bath lotions often contain moisturizing ingredients that help to keep the skin soft and hydrated, leaving it feeling refreshed and rejuvenated after bathing.

The term "shampoo" is a hair care product designed to cleanse the scalp and hair by removing dirt, oil, and other impurities. It helps to keep the hair clean, healthy, and manageable.

The term "acne treatment" refers to a range of skincare products aimed at managing and reducing acne, a common skin condition characterized by the presence of pimples, blackheads, whiteheads, and inflammation on the skin. The goal of acne treatment is to unclog pores, reduce bacteria, decrease inflammation, and promote healing, ultimately improving the appearance and health of the skin affected by acne.

The term "burned skin" refers to skin that has been injured or damaged due to exposure to heat, chemicals, radiation, or other harmful agents.

The term "lady care" typically refers to personal hygiene products designed specifically for women's intimate care needs. These products are formulated to address the unique requirements of female genital hygiene, providing cleanliness, comfort, and freshness in the vaginal area.

According to the preferred embodiment of the present invention, the hygiene solution in a subject is men's hygiene solution. It should be noted that "men's hygiene solution" typically refers to personal care products designed specifically for men's grooming and hygiene needs. These products cater to various aspects of men's personal care routines, including body cleansing, skincare, hair care, and grooming. Men's hygiene solutions aim to promote cleanliness, freshness, and overall well-being, addressing specific concerns such as body odor, sweat, and skincare.

According to another embodiment, the invention disclosing further a complex composition of turkey tail mushroom extract—chitosan produced by the method 200 for use in the treatment of an early mortality syndrome (EMS) in shrimp as a replacement for antibiotics. It should be noted that the term "Early Mortality Syndrome (EMS)" refers to a condition observed in shrimp aquaculture, characterized by a sudden and significant mortality rate among juvenile shrimp, typically occurring within the first 20 to 30 days of cultivation. EMS is associated with various factors, including bacterial and viral infections, environmental stressors, and poor water quality.

In the present invention, the complex composition of turkey tail mushroom extract—chitosan could assist in curing Liver Cancer, specifically most effective against Liver Cancer caused by Hepatitis B and Hepatitis C, allowing the patient to make a full recovery. The extract works in tandem with the immune system, with certain compounds in the extract increasing the immune response, attacking the tumor.

In the present invention, another medical use for the complex composition of turkey tail mushroom extract—chitosan is how it can be used in the manufacturing of Haemostatic Gauze. Firstly, bleeding is stopped within the first 15 seconds after packing the open wound with the haemostatic gauze. Secondly, the extract has anti-bacterial and anti-viral properties which makes it excellent for preventing infection. Lastly, the extract itself has shown to speed up the healing process, allowing the victim to recover faster. Haemostatic Gauze are mainly used for traumatic injuries to the human body which result is massive blood loss.

In the present invention, the complex composition of turkey tail mushroom extract—chitosan could also help cure HPV infections where the infections are present along the digestive system, i.e., the body of the stomach and the esophagus, due to the anti-viral nature of the composition.

In the present invention, the complex composition of turkey tail mushroom extract—chitosan is an effective treatment for burned skin, whatever the cause. Furthermore, the composition could be configured as a skin graft for larger areas of skin damage, consisting of third degree burns, similar how to a tilapia skin graft would work, except no fish.

In the present invention, the complex composition of turkey tail mushroom extract—chitosan is mixed into a drink and consumed daily. It helps the body maintain homeostasis, resulting in users feeling more energetic, hydrated, and less prone to catching illnesses. In fact, the composition is so effective at maintaining homeostasis that it can also be used as a painkiller for headaches and for treating the common cold/flu, with strength and effects equivalent to or better than ibuprofen or paracetamol.

In the present invention, the complex composition of turkey tail mushroom extract—chitosan proves beneficial in addressing age-related joint issues. With advancing age, joints may weaken, leading to discomfort or pain as bones rub against each other. Medicinally utilized, the composition can mitigate discomfort, restore functionality, and replenish deteriorated joint health. Additionally, it serves as an effective agent for maintaining overall joint health.

In the present invention, the complex composition of turkey tail mushroom extract—chitosan is used in lotions and body wash, possessing hydrating and nourishing properties for the skin. This means that the composition, in both cream and wash forms (body wash), can effectively treat eczema until it becomes unnoticeable.

In the present invention, due to the anti-bacterial and anti-viral properties of the complex composition of turkey tail mushroom extract—chitosan, it shows great effectiveness as a hand sanitizer. Along with a more pleasant odor and skin hydration, this provides an easy alternative to the traditional alcohol-aloe vera formulation.

In the present invention, the complex composition of turkey tail mushroom extract—chitosan is capable of treating Hand Foot Mouth disease, a common ailment in children caused by a viral infection that leads to sores and ulcers.

In the present invention, the complex composition of turkey tail mushroom extract—chitosan can also be utilized in the production of pill capsules as the demand for modern medicine continues to rise.

In the present invention, the complex composition of turkey tail mushroom extract—chitosan can be used as a cleanser for both males and females. This skincare product is designed to clean, sanitize, and freshen up the most intimate areas of the human body, accommodating their differing anatomy.

In the present invention, the complex composition of turkey tail mushroom extract—chitosan expands its application to include shampoo formulations. This extract-based shampoo not only cleanses the hair but also effectively treats dandruff and reduces hair loss.

In the present invention, the complex composition of turkey tail mushroom extract—chitosan is utilized in an anti-acne treatment regimen comprising both a face wash and cream. This treatment not only addresses acne but also mitigates the adverse side effects such as pitted skin resulting from prolonged use of hydrocortisone or other corticosteroids commonly used in anti-acne medications.

In the present invention, the complex composition of turkey tail mushroom extract—chitosan not only helps treat eczema and maintain homeostasis within the body but also contributes to maintaining homeostasis on the outside of the body. The composition based body wash effectively cleanses and prevents nasty odors from forming. Additionally, it addresses imbalances in the body's microbiome, which is why some people may still experience odor even after showering, thereby eliminating this embarrassing ailment.

In the present invention, the complex composition of turkey tail mushroom extract—chitosan based mouth wash and toothpaste have similar benefits in that they treat gum disease, removes odour from cavities, removes normal oral odours, treats sores, pimples, cuts inside the mouth as well as making it an effective treatment for sore throats. The mouth wash can also be used instead of salt-water gurgling as a treatment for sore throats.

In the present invention, the complex composition of turkey tail mushroom extract—chitosan can be derived into an all natural preservative allowing for the longer storage of food and decreasing synthetic chemicals in the food supply. As a preservative, it can be applied as a topical coat allowing for produce to last longer and since it's completely safe to consume, there is no risk of anyone getting sick if they forget to wash the produce. Specifically, this has shown to be quite effective at extending life on chillies, which can spoil rather quickly without the preservative.

In the present invention, while formulating the complex composition of turkey tail mushroom extract—chitosan, there is inevitably going to be waste product. However, the wastewater in this case makes an effective fertilizer. Plants have been shown to increase in strength, yield faster growth, and produce more nutrient-dense fruits.

In the present invention, the complex composition of turkey tail mushroom extract—chitosan is utilized in dishwashing liquid formulations. One common issue with traditional dishwashing liquids is their tendency to dry out the skin on fingers, hands, and nails over time. However, the dishwashing liquid formulated with the composition does not cause harm to the hands even with prolonged use. In addition to effectively cleaning and sanitizing dishes, it also nourishes the skin on the hands and helps prevent or treat fungal infections.

According to the embodiment of the present invention, 100 kg of the turkey tail mushroom mixture is made by process 100 depending on the weight (kg) of each of the ingredients listed in detail in Table 2 including Formula 1, Formula 2, and Formula 3.

TABLE 2

Mixed ingredients to creating the turkey tail mushroom mixture according to the embodiment of the invention

| | | Weight (kg) | | |
|---|---|---|---|---|
| No. | Ingredients | Formula 1 | Formula 2 | Formula 3 |
| 1 | The first turkey tail mushroom component | 20 | 12.5 | 25 |
| 2 | The second turkey tail mushroom component | 20 | 25 | 12.5 |
| 3 | The third turkey tail mushroom component | 20 | 25 | 25 |
| 4 | The fourth turkey tail mushroom component | 20 | 25 | 12.5 |
| 5 | The fifth turkey tail mushroom component | 20 | 12.5 | 25 |

Referring analysis results of total polysaccharide content in the turkey tail mushroom mixture according to Formula 1, Formula 2, and Formula 3 listed in Table 3 below.

TABLE 3

Analysis results of total polysaccharide content in the turkey tail mushroom mixture according to Formula 1, Formula 2, and Formula 3.

| Formula | Total polysaccharide content (g/Kg) |
|---|---|
| Formula 1 | 0.28 |
| Formula 2 | 0.57 |
| Formula 3 | 0.45 |

Based on Table 3, select Formula 2 with the highest total polysaccharide content. Create the mixed fermentation solution from Formula 2 by fermenting in step 102 according to process 100 to produce the mixed fermentation solution. Refer to the analysis results of the polysaccharide krestin and polysaccharide peptide concentration of the turkey tail mushroom mixture and the mixed fermentation solution in Table 4 below.

TABLE 4

Comparison of the concentration of polysaccharide krestin and polysaccharide peptide in the turkey tail mushroom mixture and the mixed fermentation solution.

| Components | Concentration (mg/g) | Concentration ratio of the mixed fermentation solution: the turkey tail mushroom mixture (times) |
|---|---|---|
| Polysaccharide krestin | | |
| The turkey tail mushroom mixture | 0.052 | 4.5 |
| The mixed fermentation solution | 0.234 | |
| Polysaccharide peptide | | |
| The turkey tail mushroom mixture | 0.036 | 5.5 |
| The mixed fermentation solution | 0.198 | |

Referring to Table 4 for the analysis results of the components Lucidenic acid N, Lucidenic acid E2, Lucidadiol, and Ergosterol in the mixed fermentation solution.

TABLE 4

Analysis results of the components Lucidenic acid N, Lucidenic acid E2, Lucidadiol, and Ergosterol in the mixed fermentation solution

| No. | Parameter | Unit | Result |
|---|---|---|---|
| 1 | Lucidenic acid N | mg/g | 0.04 |
| 2 | Lucidenic acid E2 | mg/g | 0.02 |
| 3 | Lucidadiol | mg/g | 0.6 |
| 4 | Ergosterol | mg/g | 3.3 |

According to the embodiment of the present invention, 100 kg of the complex composition of turkey tail mushroom extract—chitosan is made by method 200 depending on the weight (kg) of each of the ingredients listed in detail in Table 5 including Formula 1, Formula 2, and Formula 3.

TABLE 5

Mixed ingredients to creating the complex composition of turkey tail mushroom extract-chitosan according to the embodiment of the invention

| No. | Ingredients | Weight (kg) | | |
| --- | --- | --- | --- | --- |
| | | Formula 1 | Formula 2 | Formula 3 |
| 1 | The turkey tail mushroom extract ingredient | 59.88 | 54.89 | 44.91 |
| 2 | The emulsifier ingredient | 0.12 | 0.11 | 0.09 |
| 3 | The chitosan solution ingredient | 40 | 45 | 55 |

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method for producing a complex composition of turkey tail mushroom (*Trametes versicolor*) extract—chitosan comprising steps performed in the following specific order:
   (i) preparing materials including: a chitosan solution ingredient, a turkey tail mushroom (*Trametes versicolor*) extract ingredient, and an emulsifier ingredient;
      wherein the emulsifier ingredient is selected from the group consisting of sucrose ester, monoglyceride, triglyceride, and lecithin;
      wherein the chitosan solution ingredient is obtained by performing steps (A) to (C), comprising:
   (A) preparing materials including: a chitosan component, an acetic acid solution 95%, and a water; wherein the chitosan component has a minimum deacetylation degree of 85%;
   (B) mixing the chitosan component with the water in a ratio of 1:(20-30), stirring at 150-200 rpm for 30-40 minutes at 25° C.-35° C. to obtain a first temporary mixture; and
   (C) mixing the first temporary mixture with the acetic acid solution 95% in a ratio of 1:(60-70), stirring at 100-120 rpm for 12-16 hours at 25° C.-35° C. to obtain the chitosan solution ingredient;
      wherein the turkey tail mushroom (*Trametes versicolor*) extract ingredient obtained by performing steps (i') to (vi'), comprising:
   (i') preparing materials including: a fermentation microorganism solution and a turkey tail mushroom (*Trametes versicolor*) mixture;
      wherein the fermentation microorganism solution is obtained by mixing a first nutrient broth solution with a second nutrient broth solution and a third nutrient broth solution in a ratio of (1-3):(1-3):(1-3);
      in which, prepare each nutrient broth solution by performing in a specific order from (A') to (C') comprising:
   (A') activating a microorganism strain on the Man Rogosa Sharpe (MRS) medium, incubating at a temperature of 30° C.-35° C. for a period of 36-48 hours to obtain an activated microorganism strain;
   (B') inoculating a single colony of the activated microorganism strain into a test tube containing 10 ml of LB medium, shaking at 150-200 rpm for 22-24 hours at 30° C.-35° C. to obtain an increased biomass solution; and
   (C') inoculating the increased biomass solution into LB medium at a ratio of (1-3):100, shaking at 150-200 rpm for 22-24 hours at 30° C.-35° C. to obtain the nutrient broth solution;
      wherein the turkey tail mushroom (*Trametes versicolor*) mixture is obtained by mixing a first turkey tail mushroom (*Trametes versicolor*) component with a second turkey tail mushroom (*Trametes versicolor*) component, a third turkey tail mushroom (*Trametes versicolor*) component, a fourth turkey tail mushroom (*Trametes versicolor*) component, and a fifth turkey tail mushroom (*Trametes versicolor*) component in a ratio of (1-2):(1-2):(1-2):(1-2):(1-2), then adjusting the brix to achieve 15-20° Bx;

in which, prepare each turkey tail mushroom (*Trametes versicolor*) component by performing in a specific order from (a) to (f) comprising:
(a) selecting a mature fruiting body of the turkey tail mushroom (*Trametes versicolor*);
(b) harvesting mushroom tissue from the mature fruiting body of the turkey tail mushroom (*Trametes versicolor*) with an area ranging from 5-10 mm$^2$, inoculating onto a petri dish containing a isolation medium, and then incubating in darkness at 28° C.-30° C. for 4-6 days to obtain a turkey tail mushroom (*Trametes versicolor*) strain;
wherein the isolation medium comprising: potatoes having 200 g/L, glucose having 20 g/L, potassium dihydrogen phosphate (KH$_2$PO$_4$) having 3 g/L, magnesium sulfate (MgSO$_4$) having 1.5 g/L, and agar having 20 g/L;
(c) inoculating the turkey tail mushroom (*Trametes versicolor*) strain into an erlenmeyer flask containing 100-150 mL of an activation medium, shaking at 120-150 rpm for 4-6 days at 25° C.-27° C. to obtain an activated turkey tail mushroom (*Trametes versicolor*) strain;
wherein the activation medium comprising: glucose having 10 g/L, malt extract having 3 g/L, peptone having 2 g/L, yeast extract having 2 g/L, asparagine having 1 g/L, potassium dihydrogen phosphate (KH$_2$PO$_4$) having 2 g/L, magnesium sulfate (MgSO$_4$) having 1 g/L, and thiamine having 1 mg/L;
(d) inoculating the activated turkey tail mushroom (*Trametes versicolor*) strain into a biomass growth medium at a ratio of (1-5):1000, cultivating with agitation at 120-150 rpm for 6-8 days at 25° C.-27° C. to obtain a second temporary mixture;
wherein the biomass growth medium comprising: glucose having 30 g/L, peptone having 4 g/L, magnesium sulfate (MgSO$_4$) having 0.5 g/L, and potassium dihydrogen phosphate (KH$_2$PO$_4$) having 1 g/L;
(e) filtering the second temporary mixture, removing the liquid portion to obtain a turkey tail mushroom (*Trametes versicolor*) biomass; and
(f) drying the turkey tail mushroom (*Trametes versicolor*) biomass at 45° C.-50° C. until reaching a moisture content of 10-12% to obtain the turkey tail mushroom (*Trametes versicolor*) component;
(ii') creating a mixed fermentation solution and a mixed fermentation residue by performing steps (a') to (l'), comprising:
(a') sterilizing the turkey tail mushroom (*Trametes versicolor*) mixture at step (i') at a temperature of 121° C. for 15 minutes to obtain a third temporary mixture;
(b') mixing the fermentation microorganism solution at step (i') with the third temporary mixture in a ratio of 1:(45-55); then fermenting at 30° C.-35° C., combined stirring at a speed of 120 rpm for 35-40 hours to obtain a first fermentation mixture;
(c') filtering the first fermentation mixture to obtain a first fermentation solution and a first fermentation residue; wherein the first fermentation solution is the liquid part and the first fermentation residue is the solid part;
(d') centrifuging the first fermentation solution at a speed of 4000-6000 rpm for 60-90 minutes to obtain a first centrifuged fermentation solution and a second fermentation residue;
(e') mixing the first fermentation residue with the second fermentation residue, then adjusting the Brix to reach 15-20° Bx to obtain a basic mixture;
(f') sterilizing the basic mixture at 121° C. for 15 minutes to obtain a sterile basic mixture;
(g') mixing the fermentation microorganism solution at step (i') with the sterilized basic mixture in a ratio of 1:(45-55); then fermenting at 30° C.-35° C., combined stirring at a speed of 120 rpm for 24-30 hours to obtain a second fermentation mixture;
(h') filtering the second fermentation mixture to obtain a second fermentation solution and a third fermentation residue; wherein the second fermentation solution is the liquid part, and the third fermentation residue is the solid part;
(j') centrifuging the second fermentation solution at a speed of 4000-6000 rpm for 60-90 minutes to obtain a second centrifuged fermentation solution and a fourth fermentation residue;
(k') mixing the first centrifuged fermentation solution with the second centrifuged fermentation solution to obtain the mixed fermentation solution;
(l') mixing the first fermentation residue with the second fermentation residue, the third fermentation residue, and the fourth fermentation residues to obtain the mixed fermentation residue;
(iii') creating a mixed water-extracted solution and a mixed water-extracted residue from the mixed fermentation residue by performing steps (a") to (d"), comprising:
(a") mixing the mixed fermentation residue at step (ii') with water in a ratio of 1:(5-7), boiling at 100° C. for 10-15 minutes, then filtering to obtain a first water-extracted solution and a first water-extracted residue;
(b") mixing the first water-extracted residue with water in a ratio of 1:(5-7), boiling at 100° C. for 10-15 minutes, then filtering to obtain a second water-extracted solution and a second water-extracted residue;
(c") mixing the first water-extracted solution with the second water-extracted solution to obtain the mixed water-extracted solution; and
(d") mixing the first water-extracted residue with the second water-extracted residue to obtain the mixed water-extracted residue;
(iv') preparing an alkaline-extracted solution by performing steps (a''') to (e'''), comprising:
(a''') mixing the mixed water-extracted residue at step (iii') with 4% sodium hydroxide (NaOH) in a ratio of 1:(7-8), incubating at 55° C. for 2-3 hours, then filtering to obtain a first alkaline solution and a first alkaline residue;
(b''') mixing the first alkaline residue with 4% sodium hydroxide (NaOH) in a ratio of 1:(7-8), incubating at 55° C. for 2-3 hours, then filtering to obtain a second alkaline solution and a second alkaline residue;

(c''') mixing the first alkaline solution with the second alkaline solution to obtain a mixed alkaline solution;

(d''') neutralizing the mixed alkaline solution with 1N hydrochloric acid (HCl) until the pH reaches 6.8-7.2, then allowing for 12-16 hours to obtain a fourth temporary mixture; and (e''') filtering the fourth temporary mixture, removing the precipitate to obtain the alkaline-extracted solution;

(v') creating a turkey tail mushroom (*Trametes versicolor*) extract sediment by performing steps (a'''') to (d''''), comprising:

(a'''') mixing the fermentation mixture at step (ii'') with the mixed water-extracted solution at step (iii'') and the alkaline-extracted solution at step (iv'') to obtain a fifth temporary mixture;

(b'''') evaporating the fifth temporary mixture at 70° C. until the volume is reduced by 8-10 times to obtain a concentrated mixture;

(c'''') mixing the concentrated mixture with 96% ethanol solution in a ratio of 1:(3-5), precipitating at 4° C. for 12-16 hours to obtain a precipitated concentrated mixture; and (d'''') centrifuging the precipitated concentrated mixture at a speed of 4000-6000 rpm for 30-50 minutes, removing the liquid phase to obtain the turkey tail mushroom (*Trametes versicolor*) extract sediment;

(vi') mixing the turkey tail mushroom (*Trametes versicolor*) extract sediment at step (v') with water in a ratio of 1:(20-30) to obtain the turkey tail mushroom (*Trametes versicolor*) extract ingredient;

(ii) mixing the turkey tail mushroom (*Trametes versicolor*) extract ingredient with the emulsifier ingredient in a ratio of 1000:(1-3), stirring at a speed of 1200-1500 rpm for 30-50 minutes to obtain a first homogeneous mixture;

(iii) mixing the first homogeneous mixture with the chitosan solution ingredient in a ratio of (4-6):(4-6), stirring at a speed of 1200-1500 rpm for 30-50 minutes to obtain a second homogeneous mixture; and (iv) sonicating the second homogeneous mixture at 0.15-0.2 kHz, combined with stirring at a speed of 1200-1500 rpm for 30-40 minutes to obtain the complex composition of turkey tail mushroom (*Trametes versicolor*) extract—chitosan.

2. The method of claim 1, wherein at step (A') the microorganism strain used for preparing the first nutrient broth solution is *Lactobacillus plantarum* (with a designated identifier in the gene bank being JQ937330.1).

3. The method of claim 1, wherein at step (A') the microorganism strain used for preparing the second nutrient broth solution is *Lactobacillus acidophilus* (with a designated identifier in the gene bank being OK398226.1).

4. The method of claim 1, wherein at step (A') the microorganism strain used for preparing the third nutrient broth solution is *Bacillus subtilis* (with a designated identifier in the gene bank being KY777343.1).

5. The method of claim 1, wherein at step (a) the mature fruiting body used for preparing the first turkey tail mushroom component is *Trametes versicolor* (L.) Pilat.

6. The method of claim 1, wherein at step (a) the mature fruiting body used for preparing the second turkey tail mushroom component is *Trametes versicolor* (L.) Lioud (1920).

7. The method of claim 1, wherein at step (a) the mature fruiting body used for preparing the third turkey tail mushroom component is *Trametes sanguinea* (L.) Imazeki.

8. The method of claim 1, wherein at step (a) the mature fruiting body used for preparing the fourth turkey tail mushroom component is *Trametes versicolor* BRG04.

9. The method of claim 1, wherein at step (a) the mature fruiting body used for preparing the fifth turkey tail mushroom component is *Pycnoporus sanguineus* (L.: Fr.) Murrill.

10. The method of claim 1, wherein at step (i) the fermentation microorganism solution comprising *Lactobacillus plantarum* having at least $1\times10^9$ CFU/mL, *Lactobacillus acidophilus* having at least $1\times10^9$ CFU/mL, and *Bacillus subtilis* having at least $1\times10^9$ CFU/mL.

11. The method of claim 1, wherein at step (i) the ratio of the first turkey tail mushroom (*Trametes versicolor*) component with the second turkey tail mushroom (*Trametes versicolor*) component, the third turkey tail mushroom (*Trametes versicolor*) component, the fourth turkey tail mushroom (*Trametes versicolor*) component, and the fifth turkey tail mushroom (*Trametes versicolor*) component is 1:2:2:2:1.

12. The method of claim 1, wherein at step (i') the turkey tail mushroom (*Trametes versicolor*) mixture containing at least 0.2 g/Kg polysaccharide including polysaccharide krestin, and polysaccharide peptide.

13. The method of claim 1, wherein at step (i) the mixed fermentation solution containing polysaccharide having a concentration is 4-6 times higher than the turkey tail mushroom (*Trametes versicolor*) mixture; in which said polysaccharide including polysaccharide krestin, and polysaccharide peptide.

14. The method of claim 13, wherein at step (i) the mixed fermentation solution containing polysaccharide krestin having a concentration is 4-6 times higher than the turkey tail mushroom (*Trametes versicolor*) mixture.

15. The method of claim 13, wherein at step (i) the mixed fermentation solution containing polysaccharide peptide having a concentration is 4-6 times higher than the turkey tail mushroom (*Trametes versicolor*) mixture.

16. The method of claim 13, wherein at step (i) the mixed fermentation solution comprising further lucidenic acid N having 0.03-0.05 mg/g, lucidenic acid E2 having 0.01-0.03 mg/g, lucidadiol having 0.4-0.8 mg/g, and ergosterol having 2.2-4.6 mg/g.

\* \* \* \* \*